United States Patent
Xie (10) Patent No.: US 10,354,393 B2
(45) Date of Patent: Jul. 16, 2019

(54) METHOD AND DEVICE FOR DETERMINING MOTION TRAJECTORY OF TARGET SUBJECT, AND STORAGE MEDIUM

(71) Applicant: Tencent Technology (Shenzhen) Company Limited, Shenzhen, Guangdong (CN)

(72) Inventor: Siyuan Xie, Guangdong (CN)

(73) Assignee: Tencent Technology (Shenzhen) Company Limited, Shenzhen, Guangdong (KR)

( * ) Notice: Subject to any disclaimer, the term of this patent is extended or adjusted under 35 U.S.C. 154(b) by 106 days.

(21) Appl. No.: 15/624,245

(22) Filed: Jun. 15, 2017

(65) Prior Publication Data
US 2017/0287142 A1  Oct. 5, 2017

Related U.S. Application Data (63) Continuation of application No. PCT/CN2016/081694, filed on May 11, 2016.

(30) Foreign Application Priority Data
Jun. 24, 2015  (CN) .......................... 2015 1 0354868

(51) Int. Cl.
*G06T 7/20* (2017.01)
*A63F 13/215* (2014.01)
(Continued)

(52) U.S. Cl.
CPC .............. *G06T 7/20* (2013.01); *A63F 13/215* (2014.09); *A63F 13/2145* (2014.09);
(Continued)

(58) Field of Classification Search
CPC ... G06T 7/20; G06T 3/20; G06T 2207/20081; G06T 2207/30241; A63F 13/2145;
(Continued)

(56) References Cited

U.S. PATENT DOCUMENTS 6,115,051 A   9/2000  Simons et al.
7,477,988 B2  1/2009  Dorum
(Continued)

FOREIGN PATENT DOCUMENTS

CN   101822545 A   9/2010
CN   102201122 A   9/2011
(Continued)

OTHER PUBLICATIONS

Christopher Twigg, "Catmull-Rom splines", Mar. 11, 2003. pp. 1-3. (Year: 2003) https://www.cs.cmu.edu/~462/projects/assn2/assn2/catmullRom.pdf.*
(Continued)

*Primary Examiner* — Chong Wu
(74) *Attorney, Agent, or Firm* — Harness, Dickey & Pierce, P.L.C.

(57) ABSTRACT

A method and device for determining a motion trajectory of a target subject are provided. The method includes: acquiring a first control point and a second control point on a motion track based on a current position of the target object on the motion track, where the first control point and the second control point are adjacent control points; acquiring a first direction vector and a second direction vector, where the first direction vector is a unit direction vector at the first control point, and the second direction vector is a unit direction vector at the second control point; and determining the motion trajectory of the target object on the motion track through a specified spline curve interpolation model, based
(Continued)

on the first control point, the second control point, the first direction vector and the second direction vector.

17 Claims, 6 Drawing Sheets

(51) Int. Cl.
  *A63F 13/25* (2014.01)
  *A63F 13/35* (2014.01)
  *A63F 13/52* (2014.01)
  *G06T 3/20* (2006.01)
  *A63F 13/573* (2014.01)
  *A63F 13/2145* (2014.01)
  *A63F 13/822* (2014.01)
  *G16H 20/30* (2018.01)
(52) U.S. Cl.
  CPC .............. *A63F 13/25* (2014.09); *A63F 13/35* (2014.09); *A63F 13/52* (2014.09); *A63F 13/573* (2014.09); *G06T 3/20* (2013.01); *A63F 13/822* (2014.09); *G06T 2207/20081* (2013.01); *G06T 2207/30241* (2013.01); *G16H 20/30* (2018.01)
(58) Field of Classification Search
  CPC ........ A63F 13/215; A63F 13/25; A63F 13/35; A63F 13/52; A63F 13/573; A63F 13/822; G06F 19/00
  See application file for complete search history.

(56) References Cited

U.S. PATENT DOCUMENTS

| | | | | |
|---|---|---|---|---|
| 7,805,442 | B1* | 9/2010 | Joshi | ............... G01C 21/32 701/532 |
| 8,359,156 | B2 | 1/2013 | Guo et al. | |
| 2007/0288158 | A1 | 12/2007 | Dorum | |
| 2008/0262721 | A1 | 10/2008 | Guo et al. | |
| 2015/0325016 | A1* | 11/2015 | Carr | ............... G06T 11/20 345/442 |

FOREIGN PATENT DOCUMENTS

| | | | |
|---|---|---|---|
| CN | 102467587 | A | 5/2012 |
| CN | 102794767 | A | 11/2012 |
| CN | 103793933 | A | 5/2014 |
| CN | 103902086 | A | 7/2014 |
| CN | 105046059 | A | 11/2015 |
| JP | H10134203 | A | 5/1998 |
| JP | 2007316654 | A | 12/2007 |
| JP | 2008267875 | A | 11/2008 |
| JP | 2009294446 | A | 12/2009 |

OTHER PUBLICATIONS

Office Action regarding Korean Patent Application No. 10-2017-7016338, dated Jul. 13, 2018. Translation provided by Unitalen Attorneys at Law.
Tony D. DeRose and Brian A. Barsky. "Geometric Continuity, Shape Parameters, and Geometric Constructions for Catmull-Rom Splines." ACM Transactions on Graphics, vol. 7, No. 1. Jan. 1988. pp. 1-41.
Office Action regarding Japanese Patent Application No. 2017-538656, dated Jun. 4, 2018. Translation provided by Unitalen Attorneys at Law.
Michiko Watanabe et al. "Study of the Optimum Interpolation of Curved Lines and Surfaces based on Kullback Divergence Criterion (The Fifth Report)—The Optimum Interpolation of B-spline Curved Surfaces." Papers of 1993. The Japan Society for Precision Engineering Spring Meeting. The Japan Society for Precision Engineering. May 25, 2009. pp. 669-670.
Hiroyuki Ogata et al. "Trajectory Planning for Mobile Robots in Time-Varying Environments Considering User's Specifications." Journal of the Robotics Society of Japan. vol. 12, No. 6. The Robotics Society of Japan. Sep. 15, 1994. pp. 127-132.
Byunggu Yu et al. "Curve-Based Representation of Moving Object Trajectories." Proceedings of the International Database Engineering and Applications Symposium. Jul. 9, 2007. pp. 419-425.
International Search Report of the ISA, Haidian District, Beijing, for Application No. PCT/CN2016/081694 dated Jun. 28, 2016.
First Chinese Office Action regarding Application No. 201510354868.6 dated Jun. 7, 2016. English translation.

* cited by examiner

METHOD AND DEVICE FOR DETERMINING MOTION TRAJECTORY OF TARGET SUBJECT, AND STORAGE MEDIUM

The application is a continuation of International Patent Application No. PCT/CN2016/081694 filed on May 11, 2016, which claims the priority to Chinese Patent Application No. 201510354868.6, titled "METHOD AND DEVICE FOR DETERMINING GAME MOTION TRAJECTORY", filed on Jun. 24, 2015 with the State Intellectual Property Office of the People's Republic of China, both of which are incorporated herein by reference in their entireties.

TECHNICAL FIELD

The present disclosure relates to the field of computer technology, and in particular to a method for determining a motion trajectory of a target object, a device for determining a motion trajectory of a target object, and a storage medium.

BACKGROUND

With the rapid development of network technology, more and more mobile gaming applications are developed, such as various parkour games. When using such an application, a user may select a role in the application, which may be called as a target object. Based on the control of the user on the target object, a terminal may determine a motion trajectory of the target object on a motion track, thereby controlling the target object motion through a navigation module of the application.

SUMMARY

A method for determining a motion trajectory of a target object, a device for determining a motion trajectory of a target object, and a storage medium are provided according to embodiments of the present disclosure.

In one embodiment of the present disclosure, a method for determining a motion trajectory of a target object is provided. The method includes:

acquiring a first control point and a second control point on a motion track based on a current position of the target object on the motion track, where the first control point and the second control point are adjacent control points;

acquiring a first direction vector and a second direction vector, where the first direction vector is a unit direction vector at the first control point, and the second direction vector is a unit direction vector at the second control point; and determining the motion trajectory of the target object on the motion track through a specified spline curve interpolation model, based on the first control point, the second control point, the first direction vector and the second direction vector.

In another embodiment of the present disclosure, a device for determining a motion trajectory of a target object is provided. The device includes: one or more processors and a storage medium in which operation instructions are stored. When the operation instructions stored in the storage medium are executed, the one or more processors perform the following steps.

Based on a current position of a target object on a motion track, a first control point and a second control point on the motion track are acquired. The first control point and the second control point are adjacent control points.

A first direction vector and a second direction vector are acquired. The first direction vector is a unit direction vector at the first control point, and the second direction vector is a unit direction vector at the second control point.

Based on the first control point, the second control point, the first direction vector and the second direction vector, the motion trajectory of the target object on the motion track is determined through a specified spline curve interpolation model.

In yet another embodiment of the present disclosure, a non-instantaneous computer readable storage medium is provided. The non-instantaneous computer readable storage medium stores computer executable instructions. When executing the executable instructions, a computer performs the following steps.

Based on a current position of a target object on a motion track, a first control point and a second control point on the motion track are acquired. The first control point and the second control point are adjacent control points.

A first direction vector and a second direction vector are acquired. The first direction vector is a unit direction vector at the first control point, and the second direction vector is a unit direction vector at the second control point.

Based on the first control point, the second control point, the first direction vector and the second direction vector, a motion trajectory of the target object on the motion track is determined through a specified spline curve interpolation model.

With the technical solutions according to the embodiments of the present disclosure, in the case that the actual motion trajectory of the target object is a straight line, the first direction vector is equal to the second direction vector, multi-power variables in the specified spline curve interpolation model are cancelled, and the generated actual motion trajectory of the target object is a straight line, instead of a curve, such that the actual motion trajectory of the target object is the same as a theoretical motion trajectory, thereby improving the accuracy of the determined motion trajectory of the target object.

DETAILED DESCRIPTION OF THE EMBODIMENTS

The embodiments of the present disclosure will be described in detail as follows in conjunction with the accompany drawings, so that the purposes, characters and advantages of the present disclosure can be clearer.

Figure 1:
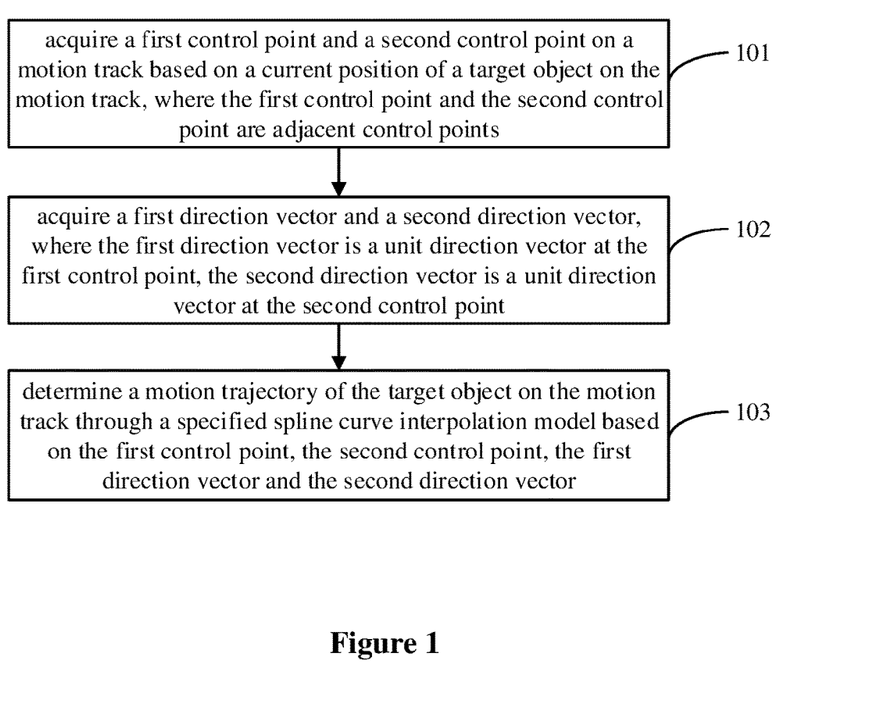
FIG. 1 is a flow chart of a method for determining a motion trajectory of a target object according to an embodiment of the present disclosure.

FIG. 1 is a flow chart of a method for determining a motion trajectory of a target object according to an embodiment of the present disclosure. The method may be applied to a terminal, which may be a mobile phone, a tablet personal computer, and a palmtop computer. Referring to FIG. 1, the method includes steps 101 to 103.

In step 101, based on a current position of a target object on a motion track, a first control point and a second control point on the motion track are acquired. The first control point and the second control point are adjacent control points.

In step 102, a first direction vector and a second direction vector are acquired. The first direction vector is a unit direction vector at the first control point, the second direction vector is a unit direction vector at the second control point.

In step 103, based on the first control point, the second control point, the first direction vector and the second direction vector, the motion trajectory of the target object on the motion track is determined through a specified spline curve interpolation model.

With the technical solutions according to the embodiments of the present disclosure, in the case that the actual motion trajectory of the target object is a straight line, the first direction vector is equal to the second direction vector, multi-power variables in the specified spline curve interpolation model are cancelled, and the generated actual motion trajectory of the target object is a straight line, instead of a curve, such that the actual motion trajectory of the target object is the same as a theoretical motion trajectory, thereby improving the accuracy of the determined motion trajectory of the target object.

Optionally, before the step that based on the first control point, the second control point, the first direction vector and the second direction vector, the motion trajectory of the target object on the motion track is determined through a specified spline curve interpolation model, the method may further include:

acquiring a training spline curve interpolation model;

determining a training distance, a first training vector and a second training vector based on a first training control point, a second training control point, a third training control point and a fourth training control point, where the first training control point, the second training control point, the third training control point and the fourth training control point may be arranged in the listed sequence; and determining the specified spline curve interpolation model based on the second training control point, the third training control point, the training distance, the first training vector, the second training vector and the training spline curve interpolation model.

Optionally, the determining a training distance, a first training vector and a second training vector based on a first training control point, a second training control point, a third training control point and a fourth training control point may include:

determining a distance between the second training control point and the third training control point as the training distance;

determining a unit direction vector of a line connecting the first training control point and the third training control point as the first training vector; and determining a unit direction vector of a line connecting the first training control point and the fourth training control point as the second training vector.

Optionally, the determining the specified spline curve interpolation model based on the second training control point, the third training control point, the training distance, the first training vector, the second training vector and a training spline curve interpolation model may include:

determining a parameter of the training spline curve interpolation model based on the second training control point, the third training control point, the training distance, the first training vector, and the second training vector; and determining the specified spline curve interpolation model based on the parameter of the training spline curve interpolation model and the training spline curve interpolation model.

Optionally, the step that based on the first control point, the second control point, the first direction vector and the second direction vector, the motion trajectory of the target object on the motion track is determined through a specified spline curve interpolation model may include:

determining an interpolation ratio of a current motion distance between the first control point and the second control point based on the first control point and the second control point;

determining a distance between the first control point and the second control point, to obtain a control point distance; and determining a motion trajectory of a current motion of the target object based on the first control point, the second control point, the interpolation ratio of the current motion distance between the first control point and the second control point, the control point distance, the first direction vector and the second direction vector, through the specified spline curve interpolation model as:

$$P(U)=P_{i-1}+\lambda EU+(3P_i-3P_{i-1}-\lambda F-2\lambda E)U^2+(-2P_i+2P_{i-1}+\lambda F+\lambda E)U^3.$$

In the above formula, P(U) represents the motion trajectory of the target object, U represents the interpolation ratio of the current motion distance between the first control point and the second control point, $P_{i-1}$ represents the first control point, $P_i$ represents the second control point, $\lambda$ represents the control point distance, E represents the first direction vector, and F represents the second direction vector.

Optionally, in the method, in the case that the first direction vector is equal to the second direction vector, the specified spline curve interpolation model is $P(U)=P_{i-1}+\lambda VU$, that is, the motion trajectory of the target object on the motion track is a straight line, where V represents the first direction vector or the second direction vector.

All of the above optional technical solutions may be combined in any way to form embodiments of the present disclosure, which are not described in detail herein.

Figure 2:
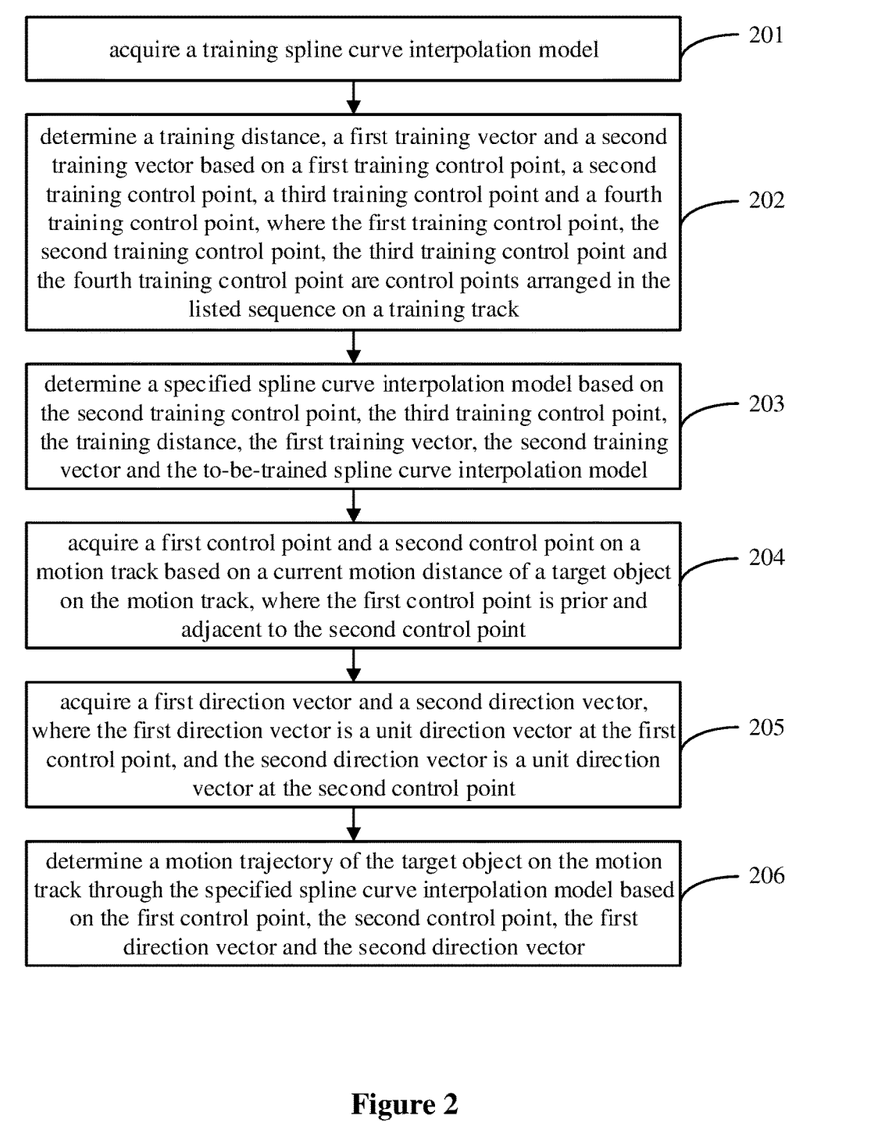
FIG. 2 is a flow chart of another method for determining a motion trajectory of a target object according to an embodiment of the present disclosure.

FIG. 2 is a flow chart of a method for determining a motion trajectory of a target object according to an embodiment of the present disclosure. The method is applied to a terminal, which may be a mobile phone, a tablet personal computer, and a palmtop computer. Referring to FIG. 2, the method includes steps 201 to 206.

In step 201, a training spline curve interpolation model is acquired.

Figure 3:
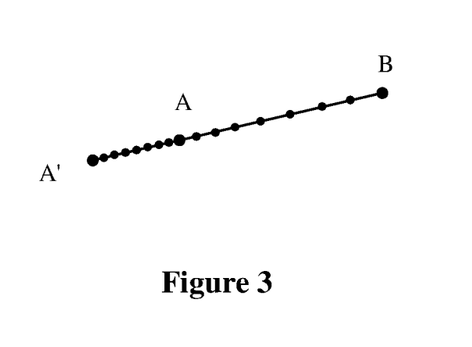
FIG. 3 is a schematic diagram of a line generated by a CatmullRom spline curve algorithm according to an embodiment of the present disclosure.

In a case that an actual motion trajectory of a target object is a straight line, a line generated through a CatmullRom spline curve algorithm is a curve, instead of a straight line. For example, as shown in FIG. 3, in the case that the actual motion trajectory of the target object is a straight line from A to B, the line generated through the CatmullRom spline curve algorithm is a line from A to A', then from A' to B. That is, the target motion object needs to first move backward from A to A' and then move from A' to B. Therefore in the embodiment according to the present disclosure, before determining the motion trajectory of the target object, a specified spline curve interpolation model may be retrained and generated such that in the case that the actual trajectory of the target object is a straight line, a line generated by the specified spline curve interpolation model is also a straight line. Before the specified spline curve interpolation model is trained, a training spline curve interpolation model is acquired.

For example, the training spline curve interpolation model may be expressed as:

$$P(U) = C_0 + C_1 U + C_2 U^2 + C_3 U^3 = \sum_{k=0}^{3} C_k U^k.$$

In the above formula, U represents an interpolation ratio and is a float between 0 to 1, P(U) represents a motion trajectory, and $C_0$, $C_1$, $C_2$ and $C_3$ represent parameters of the training spline curve interpolation model. When U is determined, P(U) represents a point on the motion trajectory. For example, when U is 0, P(0) represents a start point of the motion trajectory, and when U is 1, P(1) represents an end point of the motion trajectory.

In step 202, based on a first training control point, a second training control point, a third training control point and a fourth training control point, a training distance, a first training vector and a second training vector are determined. The first training control point, the second training control point, the third training control point and the fourth training control point are control points arranged in the listed sequence on a training track.

The specified spline curve interpolation model may be obtained based on a training motion trajectory. The first training control point, the second training control point, the third training control point and the fourth training control point are acquired. The second training control point is a start point of the training motion trajectory, the third training control point is an end point of the training motion trajectory, the first training control point is a control point prior and adjacent to the second training control point, and the fourth training control point is a control point posterior and adjacent to the third training control point. A distance between the second training control point and the third training control point is determined as the training distance. A unit direction vector of a line connecting the first training control point and the third training control point is determined as the first training vector. A unit direction vector of a line connecting the first training control point and the fourth training control point is determined as the second training vector.

For example, the first training control point is represented as $P_{i-2}$, the second training control point is represented as $P_{i-1}$, the third training control point is represented as $P_i$, and the fourth training control point is represented as $P_{i+1}$. The distance between the second training control point and the third training control point is λ, that is, the training distance is λ. The unit direction vector of the line connecting the first training control point and the third training control point is E, that is, the first training vector is E. The unit direction vector of the line connecting the first training control point and the fourth training control point is F, that is, the second training vector is F.

In step 203, based on the second training control point, the third training control point, the training distance, the first training vector, the second training vector and the training spline curve interpolation model, the specified spline curve interpolation model is determined.

When the parameters of the training spline curve interpolation model are determined, the specified spline curve interpolation model is determined based on the parameters of the training spline curve interpolation model and the training spline curve interpolation model.

As mentioned in the above step 201, P(0) represents the start point of the motion trajectory, and P(1) represents the end point of the motion trajectory. Then, for a training motion trajectory between the second training control point and the third training control point, P(0) is the second training control point $P_{i-1}$, and P(1) is the third training control point $P_i$. In addition, a direction at the second training control point is a direction of the line connecting the third training control point and the first training control point, and a direction at the third training control point is a direction of a line connecting the fourth training control point and the second training control point. In order to acquire a direction vector at the second training control point and a direction vector at the third training control point, a derivative operation is performed on the training spline curve interpolation model, to obtain a derivative model of the training spline curve interpolation model: $P'(U) = C_1 + 2C_2 U + 3C_3 U^2$. Since the direction vector at the second training control point is P'(0) and the direction vector at the third training control point is P'(1), the results $P(0) = C_0 = P_{i-1}$, $P(1) = C_0 + C_1 + C_2 + C_3 = P_i$, $P'(0) = C_1 = \lambda E$ and $P'(1) = C_1 + 2C_2 + 3C_3 = \lambda F$ are obtained. Thus, the parameters of the training spline curve interpolation model are determined as: $C_0 = P_{i-1}$, $C_1 = \lambda E$, $C_2 = 3P_i - 3P_{i-1} - \lambda F - 2\lambda E$ and $C_3 = -2P_i + 2P_{i-1} + \lambda F + \lambda E$.

Then, the parameters of the training spline curve interpolation model may be substituted into the training spline curve interpolation model, to obtain the specified spline curve interpolation model $$P(U) = P_{i-1} + \lambda E U + (3P_i - 3P_{i-1} - \lambda F - 2\lambda E)U^2 + (-2P_i + 2P_{i-1} + \lambda F + \lambda E)U^3.$$

In the formula, P(U) represents a training motion trajectory, U represents the interpolation ratio, $P_{i-1}$ represents the start point of the training motion trajectory, i.e., the second training control point, $P_i$ represents the end point of the training motion trajectory, i.e., the third training control point, λ represents the distance between the second training control point and the third training control point, i.e., the training distance, E represents the first training vector, and F represents the second training vector.

The specified spline curve interpolation model may be obtained through the training of the above steps 201 to 203. In addition, the above steps 201 to 203 may be executed not only for determining the motion trajectory of the target object, but also for obtaining the specified spline curve interpolation model. The obtained specified spline curve interpolation model may be stored. Then, in determining the motion trajectory of the target object, the specified curve spline interpolation model may be obtained directly. The embodiment of the present disclosure does not define the timing for determining the specified curve spline interpolation model. In addition, after determining the specified curve spline interpolation model, a spline curve of the target object on a motion track may be generated through the specified curve spline interpolation model, and the spline curve may include multiple control points. After that, the terminal may determine the motion trajectory of the target object on the motion track through the steps described as follows.

In step 204, a first control point and a second control point on the motion track are acquired based on a current position of the target object on the motion track, and the first control point and the second control point are adjacent control points.

In one of the embodiments of the present disclosure, the terminal may determine a motion position of the target object on the motion track at a specified time interval to obtain the motion trajectory of the target object on the motion track. The specified time interval is set in advance, for example, the specified time interval may be 1 second, such that the motion trajectory of the target object on the motion track, which is determined based on the motion position of the target object on the motion track per second, is smooth.

When the method is applied to an online game, a speed of the target object on the motion track is constant in order to ensure a display effect of the online game. Therefore, when the target object starts to move from a start point of the motion track, a current position of the target object on the motion track may be calculated based on the speed of the target object at a specific time interval. In addition, as described above, the motion track may include multiple control points, and in the embodiment of the present disclosure, for each of the multiple control points, a distance between the control point and the start point of the motion track may be calculated. The distance is divided by a total length of the motion track to obtain a length ratio of the control point. Thus, for each control point, a correspondence between the control point and a length ratio of the control point may be stored. For example, the motion track includes 10 control points, and the total length of the motion track is 100 meters. The 10 control points of a first control point to a tenth control point are respectively a start point $P_1$, $P_2$ at a distance of 10 meters, $P_3$ at a distance of 20 meters, $P_4$ at a distance of 35 meters, $P_5$ at a distance of 45 meters, $P_6$ at a distance of 60 meters, $P_7$ at a distance of 70 meters, $P_8$ at a distance of 80 meters, $P_9$ at a distance of 90 meters, and an end point $P_{10}$. That is, the distances between the start point and the ten control points of the motion track are respectively 0 meter, 10 meters, 20 meters, 35 meters, 45 meters, 60 meters, 70 meters, 80 meters, 90 meters, and 100 meters. The distances between the start point and the ten control points of the motion track are each divided by the total length of the motion track, to obtain length ratios of the ten control points, which are respectively 0%, 10%, 20%, 35%, 45%, 60%, 70%, 80%, 90%, and 100%. Then, each of the ten control points and the length ratio of each of the ten control points are stored in a correspondence table as shown in Table 1.

TABLE 1

| control point | length ratio |
|---|---|
| $P_1$ | 0% |
| $P_2$ | 10% |
| $P_3$ | 20% |

TABLE 1-continued

| control point | length ratio |
|---|---|
| $P_4$ | 35% |
| $P_5$ | 45% |
| $P_6$ | 60% |
| $P_7$ | 70% |
| $P_8$ | 80% |
| $P_9$ | 90% |
| $P_{10}$ | 100% |

The operation of acquiring a first control point and a second control point on a motion track based on a current position of the target object on the motion track may include: acquiring a distance from a start point of the target object based on the current position of the target object on the motion track, and dividing the distance by a total length of the motion track to obtain a length ratio of the current distance of the target object. Multiple length ratios stored in the correspondence table between a control point and a length ratio are obtained, and the multiple length ratios are compared with the length ratio of the current distance of the target object. Two length ratios adjacent to the length ratio of the current distance of the target object are selected from the multiple length ratios. A control point corresponding to a smaller length ratio in the selected two length ratios may be determined as the first control point, and a control point corresponding to a greater length ratio in the selected two length ratios may be determined as the second control point.

Figure 4:
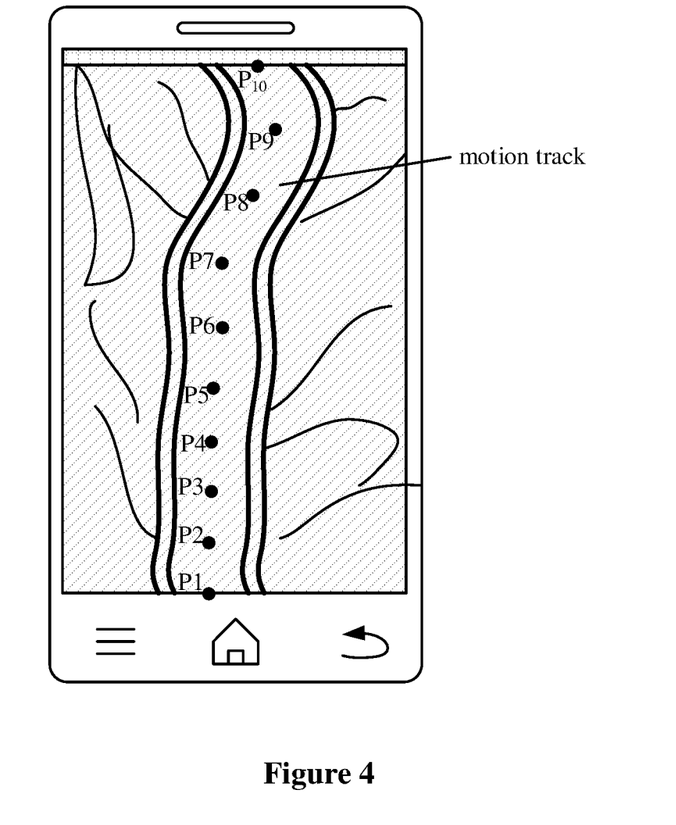
FIG. 4 is a structural diagram of an interface for determining a motion trajectory of a target object according to an embodiment of the present disclosure.

For example, in the above example, the target object has a distance of 50 meters from the start point on the motion track. The distance 50 meters is divided by the total length 100 meters of the motion track, to obtain 50% as the length ratio of the current motion distance. The multiple length ratios 0%, 10%, 20%, 35%, 45%, 60%, 70%, 80%, 90% and 100% stored in the correspondence table between a control point and a length ratio are obtained, and the multiple length ratios are compared with the length ratio of the current distance of the target object. Two length ratios 45% and 60% which are adjacent to the length ratio of the current distance of the target object are selected from the multiple length ratios. The control point $P_5$ corresponding to a smaller length ratio 45% in the selected two length ratios may be determined as the first control point, and the control point $P_6$ corresponding to a greater length ratio 60% in the selected two length ratios may be determined as the second control point. That is, as shown in FIG. 4, a fifth control point $P_5$ on the motion track is determined as the first control point, and a sixth control point $P_6$ on the motion track is determined as the second control point.

In step 205, a first direction vector and a second direction vector are acquired. The first direction vector is a unit direction vector at the first control point, and the second direction vector is a unit direction vector at the second control point.

In one of the embodiments of the present disclosure, the terminal may acquire the first direction vector and the second direction vector in various ways. For example, the derivative operation may be performed on the specified spline curve interpolation model, to obtain the derivative model of the specified spline curve interpolation model. An interpolation ratio of the first control point is calculated, and the interpolation ratio of the first control point is substituted into the specified spline curve interpolation model to obtain the first direction vector. Similarly, an interpolation ratio of the second control point is calculated, and the interpolation ratio of the second control point is substituted into the specified spline curve interpolation model to obtain the second direction vector. For another example, based on coordinates of the second control point and coordinates of a third control point, a unit direction vector of a line connecting the second control point and the third control point may be calculated, to obtain the first direction vector. The third control point is a control point prior and adjacent to the first control point. Similarly, based on coordinates of a fourth control point and coordinates of the first control point, a unit direction vector of a line connecting the fourth control point and the first control point may be calculated, to obtain the second direction vector. The fourth control point is a control point posterior and adjacent to the second control point. The various ways for acquiring the first direction vector and the second direction vector are not listed in embodiments of the present disclosure.

In one of the embodiments of the present disclosure, the method for calculating the interpolation ratio of the first control point and the interpolation ratio of the second control point is the same as the method for calculating the interpolation ratio of a current distance of the target object between the first control point and the second control point, which is described in detail in step 206 and is not described here. In addition, the method for obtaining the first direction vector by calculating the unit direction vector of the line connecting the second control point and the third control point based on the coordinates of the second control point and the coordinates of the third control point may include: subtracting the coordinates of the third control point from the coordinates of the second control point, to obtain a direction vector between the second control point and the third control point, and unitizing the direction vector between the second control point and the third control point to obtain the first direction vector. The method for calculating the second direction vector is similar, which is not described in detail herein.

In step 206, based on the first control point, the second control point, the first direction vector and the second direction vector, the motion trajectory of the target object on the motion track is determined through the specified spline curve interpolation model.

The terminal determines an interpolation ratio of a current distance of the target object between the first control point and the second control point based on the first control point and the second control point, determines a distance between the first control point and the second control point to obtain a control point distance, and determines a motion trajectory of a current motion of the target object based on the first control point, the second control point, the interpolation ratio of the current distance of the target object between the first control point and the second control point, the control point distance, the first direction vector and the second direction vector, through the specified spline curve interpolation ratio as:

$$P(U)=P_{i-1}+\lambda EU+(3P_i-3P_{i-1}-\lambda F-2\lambda E)U^2+(-2P_i+2P_{i-1}+\lambda F+\lambda E)U^3.$$

In the above formula, P(U) represents a motion trajectory of the target object, U represents the interpolation ratio of the current distance of the target object between the first control point and the second control point, $P_{i-1}$ represents a start point of the motion trajectory of the current motion of the target object, i.e., the first control point, $P_i$ represents an end point of the motion trajectory of the current motion of the target object, i.e., the second control point, λ represents the distance between the first control point and the second control point, i.e., the control point distance, E represents the unit direction vector at the first control point, i.e., the first direction vector, and F represents the unit direction vector at the second control point, i.e., the second direction vector.

A specific operation of the terminal for determining an interpolation ratio of a current distance of the target object between the first control point and the second control point based on the first control point and the second control point may include: subtracting a length ratio of the first control point from a length ratio of the current distance of the target object to obtain a first ratio, subtracting the length ratio of the first control point from a length ratio of the second control point to obtain a second ratio, and dividing the first ratio by the second ratio to obtain the interpolation ratio of the current distance of the target object between the first control point and the second control point.

In addition, the control point distance may be calculated based on the coordinates of the first control point and the coordinates of the second control point. For detailed calculation method, reference may be made to the related existing technology, which is not described in detail herein.

Figure 5:
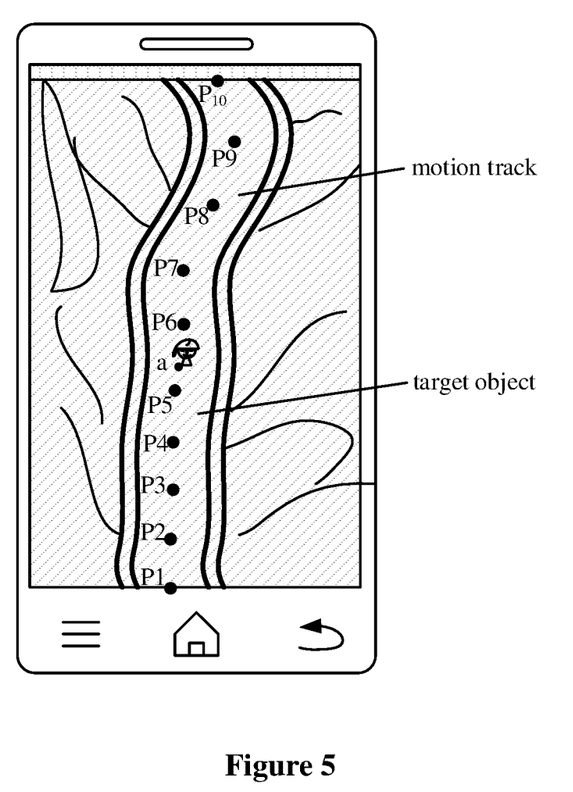
FIG. 5 is a structural diagram of another interface for determining a motion trajectory of a target object according to an embodiment of the present disclosure.

For example, the length ratio 45% of the first control point $P_5$ is subtracted from the length ratio 50% of the current distance of the target object to obtain the first ratio as 5%. The length ratio 45% of the first control point $P_5$ is subtracted from the length ratio 60% of the second control point $P_6$ to obtain the second ratio as 15%. The first ratio 5% is divided by the second ratio 15% to obtain the interpolation ratio of the current distance of the target object between the first control point $P_5$ and the second control point $P_6$ as 33%. If the coordinates of the first control point $P_5$ is (0, 0, 45), the coordinates of the second control point $P_6$ is (0, 0, 60), and both the first direction vector and the second direction vector is (0, 0, 1), the distance between the first control point $P_5$ and the second control point $P_6$ is calculated as 15 meters, that is, the control point distance is 15 meters. Then, based on the first control point $P_5$ (0, 0, 45), the second control point $P_6$ (0, 0, 60), the interpolation ratio 33% of the current distance of the target object between the first control point and the second control point, the control point distance 15, the first direction vector (0, 0, 1) and the second direction vector (0, 0, 1), a position of the current motion distance of the target object is determined as (0, 0, 49.95) through the above specified spline curve interpolation model, and then the motion trajectory of the target object is determined. That is, the position (0, 0, 49.95) of the current motion distance of the target object is determined as point a based on the first control point $P_1$ and the second control point $P_2$ in FIG. 4, to obtain an interface diagram shown in FIG. 5 (in practice, the control points may not be displayed).

It is to be noted that, in the case that an actual motion trajectory of the target object is a straight line, that is, in the case that the first direction vector and the second direction vector are equal, the first direction vector and the second direction vector are unified and expressed as V, the distance $P_i-P_{i-1}$ between the first control point and the second control point may be expressed as λV, and the above specified spline curve interpolation model is:

$$\begin{aligned}P(U) &= P_{i-1} + \lambda EU + (3P_i - 3P_{i-1} - \lambda F - 2\lambda E)U^2 + \\ & \quad (-2P_i + 2P_{i-1} + \lambda F + \lambda E)U^3 \\ &= P_{i-1} + \lambda VU + (3\lambda V - \lambda V - 2\lambda V)U^2 + (-2\lambda V + \lambda V + \lambda V)U^3 \\ &= P_{i-1} + \lambda VU + (3\lambda V - 3\lambda V)U^2 + (-2\lambda V + 2\lambda V)U^3 \\ &= P_{i-1} + \lambda VU\end{aligned}$$

Figure 6:
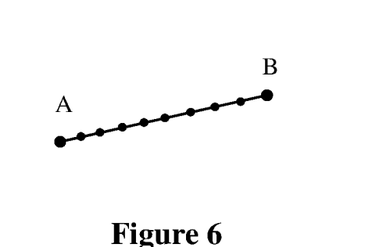
FIG. 6 is a schematic diagram of a line generated by a specified spline curve interpolation model according to an embodiment of the present disclosure.

In this case, the specified spline curve interpolation model is a straight line. Therefore, the motion trajectory of the target object cannot be a curve for any value of U from 0 to 1, thereby improving the accuracy of the determined motion trajectory. As shown in FIG. 6, in the case that the actual trajectory is a straight line from A to B, the line generated by the specified spline curve interpolation model is a line directly from A to B, and the target motion object also moves directly from A to B, without the backward moving as shown in FIG. 3.

In addition, in the case that the actual trajectory is a straight line, a change rate of a spline curve generated by a CatmullRom spline curve algorithm is not constant, that is, a motion speed of the target object determined by the CatmullRom spline curve algorithm is not constant. As shown in FIG. 3, gaps between points interpolated from A' to B change from small to large, that is, for a constant specified time interval, the speed of the target object moving between A' and B also change from slow to fast. However, in a navigation system, the motion speed of the target object needs to be constant, that is, a change rate of the spline curve must be constant. In the embodiment of the present disclosure, after the derivative operation is performed on the specified spline curve interpolation model $P(U)=P_{i-1}+\lambda VU$ in the case of the straight line, the derivative model of the specified spline curve interpolation model is obtained as $P(U)=\lambda V$, which is a constant. Therefore, through the specified spline curve interpolation model according to the embodiment of the present disclosure, the change rate of the generated spline curve is constant, that is, the motion speed of the target object is uniform, instead of an inconstant motion speed of the target object. As shown in FIG. 6, gaps of points interpolated from A to B are equal, that is, for a constant specified time interval, a speed of the target object moving between A and B is also constant.

It should be noted that, the method for determining the motion trajectory of the target object according to the embodiment of the present disclosure may be applied in a scene of a network game requiring interaction with an application server. In this case, a system for determining the motion trajectory may include a terminal and the application server. The terminal is connected with the application server through network. The terminal may determine the motion trajectory of the target object with the above method, and may synchronize the motion trajectory of the target object to the application server, such that the application server performs a specified operation. For example, when the motion trajectory reaches a specified position of the motion track, the application server may reward a user corresponding to the terminal. Apparently, the method for determining the motion trajectory may also be applied in other scenes, for example, a scene in which the terminal play an online game in a standalone way, that is, the system for determining the motion trajectory only includes the terminal. The scenes of determining a motion trajectory are not limited in the embodiments of the present disclosure.

With the technical solutions according to the embodiment of the present disclosure, in the case that the actual motion trajectory of the target object is a straight line, the first direction vector is equal to the second direction vector, multi-power variables in the specified spline curve interpolation model are cancelled, and the generated actual motion trajectory of the target object is a straight line, instead of a curve, such that the actual motion trajectory of the target object is the same as a theoretical motion trajectory, thereby improving the accuracy of the determined motion trajectory of the target object. In addition, the speed of motion on the motion trajectory determined through the specified spline interpolation model is constant, avoiding the inconstant speed of the target object.

Figure 7:
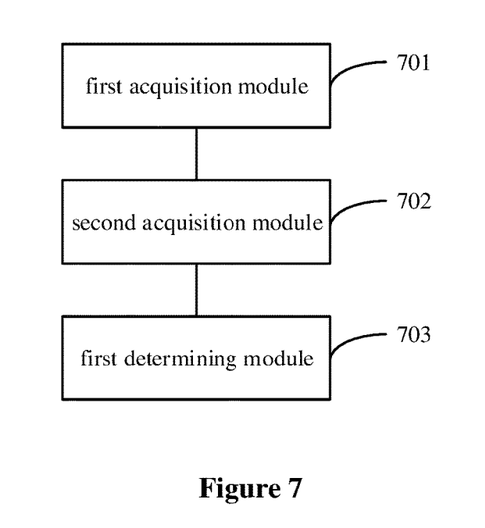
FIG. 7 is a structural schematic diagram of a device for determining a motion trajectory of a target object according to an embodiment of the present disclosure.

FIG. 7 is a software structural schematic diagram of a device for determining a motion trajectory of a target object according to an embodiment of the present disclosure. Referring to FIG. 7, the device may include a processor and a memory that stores multiple modules executable by the processor. The multiple modules include: a first acquisition module 701, a second acquisition module 702 and a first determining module 703.

The first acquisition module 701 is configured to acquire a first control point and a second control point on a motion track based on a current position of the target object on the motion track. The first control point and the second control point are adjacent control points.

The second acquisition module 702 is configured to acquire a first direction vector and a second direction vector. The first direction vector is a unit direction vector at the first control point, and the second direction vector is a unit direction vector at the second control point.

The first determining module 703 is configured to determine the motion trajectory of the target object on the motion track through a specified spline curve interpolation model based on the first control point, the second control point, the first direction vector and the second direction vector.

Figure 8:
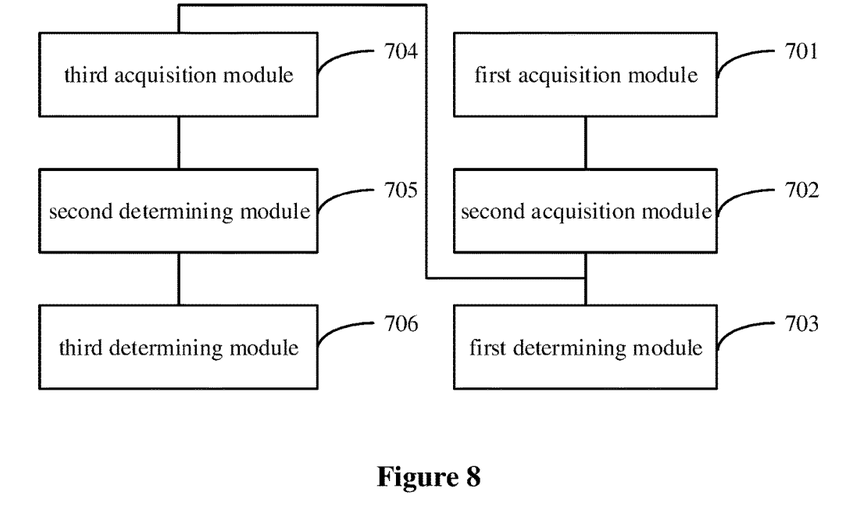
FIG. 8 is a structural schematic diagram of another device for determining a motion trajectory of a target object according to an embodiment of the present disclosure.

Optionally, referring to FIG. 8, the device may further include: a third acquisition module 704, a second determining module 705, and a third determining module 706.

The third acquisition module 704 is configured to acquire a training spline curve interpolation model.

The second determining module 705 is configured to determine a training distance, a first training vector and a second training vector based on a first training control point, a second training control point, a third training control point and a fourth training control point. The first training control point, the second training control point, the third training control point and the fourth training control point are control points arranged in the listed sequence.

The third determining module 706 is configured to determine the specified spline curve interpolation model based on the second training control point, the third training control point, the training distance, the first training vector, the second training vector and the training spline curve interpolation model.

Optionally, the second determining module 705 may include a first determining unit, a second determining unit and a third determining unit.

The first determining unit is configured to determine a distance between the second training control point and the third training control point as the training distance.

The second determining unit is configured to determine a unit direction vector of a line connecting the first training control point and the third training control point as the first training vector.

The third determining unit is configured to determine a unit direction vector of a line connecting the first training control point and the fourth training control point as the second training vector.

Optionally, the third determining module 706 may include: a fourth determining unit and a fifth determining unit.

The fourth determining unit is configured to determine a parameter of the training spline curve interpolation model based on the second training control point, the third training control point, the training distance, the first training vector and the second training vector.

The fifth determining unit is configured to determine the specified spline curve interpolation model based on the parameter of the training spline curve interpolation model and the training spline curve interpolation model.

Optionally, the first determining module 703 may include a sixth determining unit, a seventh determining unit and an eighth determining unit.

The sixth determining unit is configured to determine an interpolation ratio of a current motion position of the target object between the first control point and the second control point based on the first control point and the second control point.

The seventh determining unit is configured to determine a distance between the first control point and the second control point, to obtain a control point distance.

The eighth determining unit is configured to determine a motion trajectory of a current motion of the target object based on the first control point, the second control point, the interpolation ratio of the current motion position of the target object between the first control point and the second control point, the control point distance, the first direction vector and the second direction vector, through the specified spline curve interpolation model as:

$$P(U)=P_{i-1}+\lambda EU+(3P_i-3P_{i-1}-\lambda F-2\lambda E)U^2+(-2P_i+2P_{i-1}+\lambda F+\lambda E)U^3,$$

P(U) represents the motion trajectory of the target object, U represents the interpolation ratio of the current motion position of the target object between the first control point and the second control point, $P_{i-1}$ represents the first control point, $P_i$ represents the second control point, $\lambda$ represents the control point distance, E represents the first direction vector, and F represents the second direction vector.

Optionally, in the device, in the case that the first direction vector is equal to the second direction vector, the specified spline curve interpolation model is $P(U)=P_{i-1}+\lambda VU$, the motion trajectory of the target object on the motion track is a straight line, where V is the first direction vector or the second direction vector.

With the technical solutions according to the embodiments of the present disclosure, in the case that the actual motion trajectory of the target object is a straight line, the first direction vector is equal to the second direction vector, multi-power variables in the specified spline curve interpolation model are cancelled, and the generated actual motion trajectory of the target object is a straight line, instead of a curve, such that the actual motion trajectory of the target object is the same as a theoretical motion trajectory, thereby improving the accuracy of the determined motion trajectory of the target object.

It is to be noted that, the device for determining a game motion trajectory according to the above embodiments of the present disclosure is only illustrated with some examples of functional modules for determining the motion trajectory. In practice, the above functions may be achieved by different functional modules as needed. That is, the internal structure of the device may be designed as different functional modules to complete all or a part of the functions described above. In addition, the above embodiments of the device for determining a game motion trajectory belong to the same concept as the embodiments of the method for determining a game motion trajectory. For the detailed implementations of the device, reference may be made to the embodiments of the method, which are not repeated herein.

Figure 9:
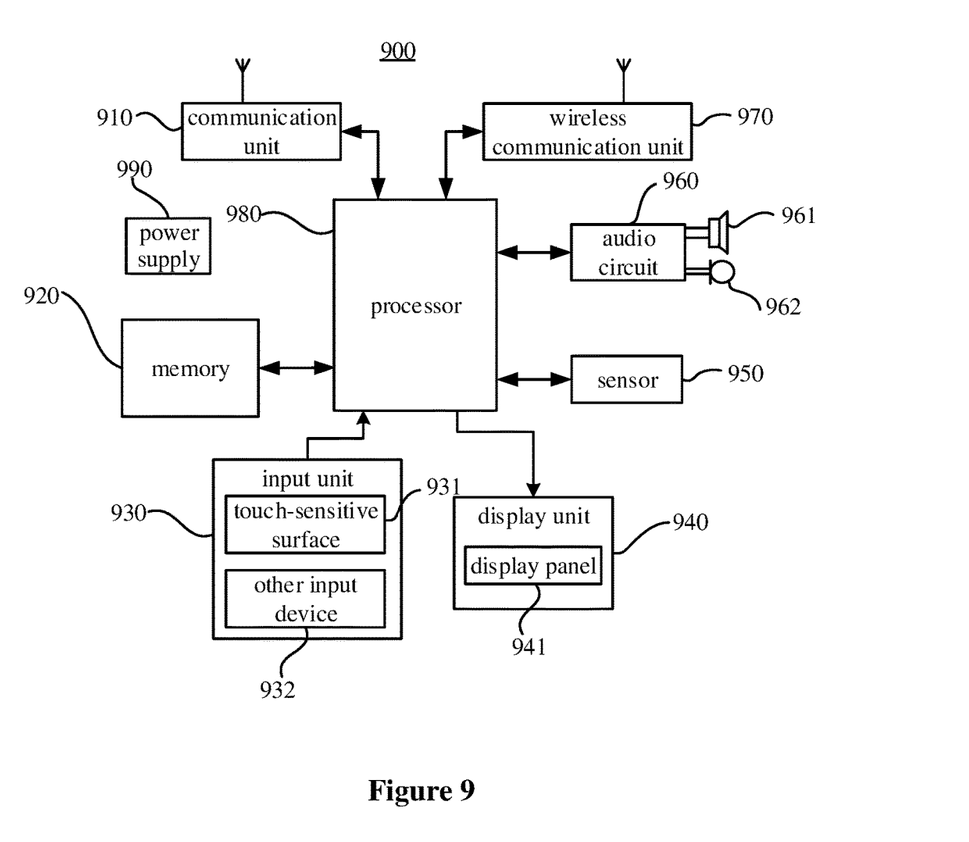
FIG. 9 is a structural schematic diagram of another device for determining a motion trajectory of a target object according to an embodiment of the present disclosure.

Referring to FIG. 9, a structural block diagram of a device for determining a motion trajectory of a target object is shown according to an embodiment of the present disclosure. The device may be a terminal 900, which may include a communication unit 910, a memory 920 which includes one or more computer readable storage mediums, an input unit 930, a display unit 940, a sensor 950, a voice-frequency circuit 960, a WiFi (Wireless Fidelity) module 970, a processor 980 which includes one or more processing cores and a power supply 990. It can be understood by those skilled in the art that the terminal structure shown in FIG. 9 does not limit the terminal. The terminal may include more or fewer components than illustrated. Some of the component may be integrated, or may be arranged differently.

The communication unit 910 may be configured to receive and send information, or to receive and send a signal in a call. The communication unit 910 may be a RF (Radio Frequency) circuit, a router, a modem, or other network communication devices. Specially, when the communication unit 910 is an RF circuit, the RF circuit delivers the downlink information received from a base station to one or more of the processors 980 for processing, and transmits related uplink data to the base station. Generally, the RF circuit, as the communication unit, includes but is not limited to an antenna, at least one amplifier, a tuner, one or more oscillators, a subscriber identity module (SIM) card, a transceiver, a coupler, an LNA (Low Noise Amplifier), and a duplexer. In addition, the communication unit 910 may further communicate with other devices and network by means of wireless communication. The wireless communication may be performed with any communication standards or protocols, including but not limited to GSM (Global System of Mobile communication), GPRS (General Packet Radio Service), CDMA (Code Division Multiple Access), WCDMA (Wideband Code Division Multiple Access), LTE (Long Term Evolution), E-mail, and SMS (Short Messaging Service). The memory 920 may be configured to store software programs and modules disclosed in FIGS. 7 and 8, and the processor 980 may execute various function applications and data processing by executing the software programs and modules stored in the memory 620. The memory 920 may mainly include a program storage area and a data storage area. The program storage area may store, for example, an operating system and an application required by at least one function (such as, an audio play function, an image display function). The data storage area may store, for example, data created in response to the use of the terminal 900 (such as, audio data, a phone book). In addition, the memory 920 may include a high-speed random access memory and a nonvolatile memory, such as at least one magnetic disk memory, and a flash memory, or include other volatile solid-state memory. Accordingly, the memory 920 may also include a storage controller to control access to the memory 920 by the processor 980 and the input unit 930.

The input unit 930 may be configured to receive inputted numeric or character information, and to generate signals related to user settings and function control inputted with a keyboard, a mouse, an operating rod, an optical or a track ball. Preferably, the input unit 930 may include a touch-sensitive surface 931 and other input device 932. The touch-sensitive surface 931, also referred to as a touch screen or a touch panel, may collect a touch operation performed by a user on or near the touch-sensitive surface 630a (for example, an operation performed on or near the touch-sensitive surface 931 by a user with a finger, a stylus pr any other suitable object or accessory), and drive corresponding connection devices based pm a preset program. Optionally, the touch-sensitive surface 931 may include both a touch detection device and a touch controller. The touch detection device detects touch position of a user, detects a signal generated from the touch operation, and sends the signal to the touch controller. The touch controller receives touch information from the touch detection device, converts the touch information into touch coordinates and sends the touch coordinates to the processor 980. The touch controller also can receive a command from the processor 980 and execute the command. In addition, the touch-sensitive surface 931 may be implemented in multiple forms such as a resistive form, a capacitive form, an infrared form, and a surface acoustic wave form. In addition to the touch-sensitive surface 931, the input unit 930 may also include other input device 932. Preferably, the other input device 932 may include but are not limited to one or more of a physical keyboard, a function key (such as a volume control button, a switch button), a trackball, a mouse and a joystick.

The display unit 940 may be configured to display information inputted by a user, information provided to the user, or various graphical user interfaces of the terminal 900. The graphical user interfaces may be constituted by graphics, texts, icons, videos and any combination thereof. The display unit 940 may include a display panel 941. Optionally, the display panel 941 may be formed in a form of a LCD (Liquid Crystal Display), an OLED (Organic Light-Emitting Diode) or the like. Further, the display panel 941 may be covered by the touch-sensitive surface 931. When the touch-sensitive surface 931 detects a touch operation thereon or thereby, the touch-sensitive surface 931 transmits the touch operation to the processor 980 to determine the type of the touch event, and then the processor 980 provides a corresponding visual output on the display panel 941 according to the type of the touch event. Although the touch-sensitive surface 931 and the display panel 941 implement the input and output functions as two separate components in FIG. 9, the touch-sensitive surface 931 and the display panel 941 may be integrated together to implement the input and output functions in other embodiments.

The terminal 900 may further include the at least one sensor 950, such as a photo sensor, a motion sensor and other sensors. The optical sensor may include an ambient light sensor and a proximity sensor. With the ambient light sensor, the luminance of the display panel 941 may be adjusted based on the intensity of ambient light. With the proximity sensor, the backlight or the display panel 941 may be turned off when the terminal 900 is approaching to the ear. As a kind of motion sensor, a gravity acceleration sensor may detect the magnitude of acceleration in each directions (usually three-axis directions) and detect the value and direction of the gravity when the sensor is in the stationary state, which may be applied in, for example, an application requiring recognition of a mobile phone gesture (for example, switching between vertical-screen and horizontal-screen, a related game, or magnetometer attitude calibration), and may be applied to an application relating to vibration recognition (for example, a pedometer, beating recognition). Other sensors such as a gyroscope, a barometer, a hygrometer, a thermometer, or an infrared sensor, may be further provided in the terminal 900, which are not described herein.

The audio circuit 960, a speaker 961 and a microphone 962 may provide an audio interface between the user and the terminal 900. The audio circuit 960 may transmit an electric signal, converted from received audio data, to the speaker 961. The electrical signal is converted into a voice signal and outputted by the speaker 961. On the other hand, the microphone 962 converts the collected voice signal into an electrical signal, and the electrical signal is received and converted into audio data by the audio circuit 960. The audio data is outputted to the processor 980 for processing and then sent to another terminal via the communication unit 910. Or the audio data is outputted to the memory 920 for further processing. The audio circuit 960 may also include an earplug jack to be used for communication between a peripheral headphone and the terminal 900.

For wireless communication, the terminal may be configured with a wireless communication unit 970, which may be a WiFi module. The WiFi technology is a short-range wireless transmission technology. The terminal 900 may assist the user to, for example, send and receive an E-mail, browse a webpage, and access a stream media via the wireless communication unit 970. The wireless communication unit 970 provides access to wireless broadband Internet for the user. Although the wireless communication unit 970 is shown in FIG. 9, it can be understood that, the wireless communication unit 970 is not a necessary unit for the terminal 900, and may be omitted as needed without departing from the essence of the present disclosure.

The processor 980 is a control center of the terminal 900, which is connected to various parts of the mobile phone through various interfaces and circuit. The processor 980 implements various functions and data processing of the terminal 900 by running or executing the software programs and/or the modules stored in the memory 920 and invoking data stored in the memory 920, to perform an overall monitoring of the mobile phone. Optionally, the processor 980 may include one or more processing cores. Preferably, an application processor and a modem processor may be integrated into the processor 980. The application processor is mainly used to process, for example, an operating system, a user interface and an application. The modem processor is mainly used to process wireless communication. It can be understood that, the above modem processor may not be integrated into the processor 980.

The terminal 900 also includes the power supply 990 (such as a battery) for supplying power to various components. Preferably, the power supply may be logically connected with the processor 980 via a power supply management system, to perform functions such as charging, discharging and power management by the power supply management system. The power supply 960 may also include one or more direct current or alternating current power supplies, a recharge system, a power failure detection circuit, a power converter or inverter, and a power supply status indicator, and other components.

Although not shown, the terminal 900 may also include a camera, a Bluetooth module and so on, which are not described herein.

In the embodiment, the terminal may further include one or more programs stored in the memory and executed by the one or more processors. The one or more programs include instructions for performing the method for determining a gaming motion trajectory according to the embodiments of the present disclosure. The instructions include:

acquiring a first control point and a second control point on a motion track based on a current position of the target object on the motion track, where the first control point and the second control point are adjacent control points;

acquiring a first direction vector and a second direction vector, where the first direction vector is a unit direction vector at the first control point, and the second direction vector is a unit direction vector at the second control point; and determining the motion trajectory of the target object on the motion track through a specified spline curve interpolation model based on the first control point, the second control point, the first direction vector and the second direction vector.

Optionally, before the determining the motion trajectory of the target object on the motion track through a specified spline curve interpolation model based on the first control point, the second control point, the first direction vector and the second direction vector, the instructions further include:

acquiring a training spline curve interpolation model;

determining a training distance, a first training vector and a second training vector based on a first training control point, a second training control point, a third training control point and a fourth training control point, where the first training control point, the second training control point, the third training control point and the fourth training control point are control points arranged in the listed sequence; and determining the specified spline curve interpolation model based on the second training control point, the third training control point, the training distance, the first training vector, the second training vector and the training spline curve interpolation model.

Optionally, the determining a training distance, a first training vector and a second training vector based on a first training control point, a second training control point, a third training control point and a fourth training control point may include:

determining a distance between the second training control point and the third training control point as the training distance;

determining a unit direction vector of a line connecting the first training control point and the third training control point as the first training vector; and determining a unit direction vector of a line connecting the first training control point and the fourth training control point as the second training vector.

Optionally, the determining the specified spline curve interpolation model based on the second training control point, the third training control point, the training distance, the first training vector, the second training vector and the training spline curve interpolation model may include:

determining a parameter of the training spline curve interpolation model based on the second training control point, the third training control point, the training distance, the first training vector, and the second training vector; and determining the specified spline curve interpolation model based on the parameter of the training spline curve interpolation model and the training spline curve interpolation model.

Optionally, the determining the motion trajectory of the target object on the motion track through a specified spline curve interpolation model based on the first control point, the second control point, the first direction vector and the second direction vector may include:

determining an interpolation ratio of a current motion position between the first control point and the second control point based on the first control point and the second control point;

determining a distance between the first control point and the second control point, to obtain a control point distance; and determining a motion trajectory of a current motion of the target object based on the first control point, the second control point, the interpolation ratio of the current motion position between the first control point and the second control point, the control point distance, the first direction vector and the second direction vector, through the specified spline curve interpolation model as:

$$P(U)=P_{i-1}+\lambda EU+(3P_i-3P_{i-1}-\lambda F-2\lambda E)U^2+(-2P_i+2P_{i-1}+\lambda F+\lambda E)U^3,$$

In the model, $P(U)$ represents the motion trajectory of the target object, U represents the interpolation ratio of the current motion position between the first control point and the second control point, $P_{i-1}$ represents the first control point, $P_i$ represents the second control point, $\lambda$ represents the control point distance, E represents the first direction vector, and F represents the second direction vector.

Optionally, in the method in the case that the first direction vector is equal to the second direction vector, the specified spline curve interpolation model is $P(U)=P_{i-1}+\lambda VU$, and the motion trajectory of the target object on the motion track is a straight line.

With the technical solutions according to the embodiments of the present disclosure, in the case that the actual motion trajectory of the target object is a straight line, the first direction vector is equal to a second direction vector, multi-power variables in a specified spline curve interpolation model are cancelled, and the generated actual motion trajectory of the target object is a straight line, instead of a curve, such that the actual motion trajectory of the target object is the same as a theoretical motion trajectory, thereby improving the accuracy for determining the motion trajectory of the target object.

It can be understood by those skilled in the art that all or some of steps according to the above embodiments may be implemented by hardware, and also may be implemented by program instructing hardware. The program may be stored in a computer readable storage medium, which may be a read-only memory, a magnetic disk or an optical disk.

The above only describes preferred embodiments according to the present disclosure, and is not intended to limit the present disclosure. Any modifications, equivalent replacements and variations made in the spirit and principle of the present disclosure fall within the scope of protection of the present disclosure.

The invention claimed is:

1. A method for determining a motion trajectory of a target object, comprising:

acquiring, by a terminal with one or more processors and a storage medium, a first control point and a second control point on a motion track based on a current position of the target object on the motion track, wherein the first control point and the second control point are adjacent control points;

acquiring, by the terminal, a first direction vector and a second direction vector, wherein the first direction vector is a unit direction vector at the first control point, and the second direction vector is a unit direction vector at the second control point;

acquiring, by the terminal, a training spline curve interpolation model;

determining, by the terminal, a training distance;

determining, by the terminal, a first unit training vector and a second unit training vector through a derivative operation on the training spline curve interpolation model based on a first training control point, a second training control point, a third training control point, and a fourth training control point, wherein the first training control point, the second training control point, the third training control point, and the fourth training control point are control points arranged in the listed sequence on a training track;

determining, by the terminal, a specified spline curve interpolation model based on the second training control point, the third training control point, the training distance, the first unit training vector, the second unit training vector, and the training spline curve interpolation model;

determining, by the terminal, the motion trajectory of the target object on the motion track through the specified spline curve interpolation model, based on the first control point, the second control point, the first direction vector, and the second direction vector; and controlling, by the terminal, motion of the target object based on the motion trajectory.

2. The method according to claim 1, wherein the determining the training distance comprises:

determining a distance between the second training control point and the third training control point as the training distance, wherein the determining the first unit training vector and the second unit training vector through the derivative operation on the training spline curve interpolation model based on the first training control point, the second training control point, the third training control point, and the fourth training control point comprises:

determining a unit direction vector of a line connecting the first training control point and the third training control point as the first unit training vector; and determining a unit direction vector of a line connecting the first training control point and the fourth training control point as the second unit training vector.

3. The method according to claim 2, wherein the determining the motion trajectory of the target object on the motion track through the specified spline curve interpolation model based on the first control point, the second control point, the first direction vector, and the second direction vector comprises:

determining an interpolation ratio of the current position of the target object between the first control point and the second control point based on the first control point and the second control point;

determining a distance between the first control point and the second control point, to obtain a control point distance; and determining, a motion trajectory of a current motion of the target object based on the first control point, the second control point, the interpolation ratio, the control point distance, the first direction vector, and the second direction vector, through the specified spline curve interpolation model as:

$P(U)=P_{i-1}+\lambda EU+(3P_i-3P_{i-1}-\lambda F-2\lambda E)U^2+(-2P_i+2P_{i-1}+\lambda F+\lambda E)U^3$, wherein P(U) is the motion trajectory of the target object, U is the interpolation ratio, $P_{i-1}$ is the first control point, $P_i$ is the second control point, λ is the control point distance, E is the first direction vector, and F is the second direction vector.

4. The method according to claim 1, wherein the determining the specified spline curve interpolation model based on the second training control point, the third training control point, the training distance, the first unit training vector, the second unit training vector, and the training spline curve interpolation model comprises:

determining a parameter of the training spline curve interpolation model based on the second training control point, the third training control point, the training distance, the first unit training vector, and the second unit training vector; and determining the specified spline curve interpolation model based on the parameter of the training spline curve interpolation model and the training spline curve interpolation model.

5. The method according to claim 4, wherein the determining the motion trajectory of the target object on the motion track through the specified spline curve interpolation model based on the first control point, the second control point, the first direction vector, and the second direction vector comprises:

determining an interpolation ratio of the current position of the target object between the first control point and the second control point based on the first control point and the second control point;

determining a distance between the first control point and the second control point, to obtain a control point distance; and determining, a motion trajectory of a current motion of the target object based on the first control point, the second control point, the interpolation ratio, the control point distance, the first direction vector, and the second direction vector, through the specified spline curve interpolation model as:

$P(U)=P_{i-1}+\lambda EU+(3P_i-3P_{i-1}-\lambda F-2\lambda E)U^2+(-2P_i+2P_{i-1}+\lambda F+\lambda E)U^3$, wherein P(U) is the motion trajectory of the target object, U is the interpolation ratio, $P_{i-1}$ is the first control point, $P_i$ is the second control point, λ is the control point distance, E is the first direction vector, and F is the second direction vector.

6. The method according to claim 1, wherein the determining the motion trajectory of the target object on the motion track through the specified spline curve interpolation model based on the first control point, the second control point, the first direction vector, and the second direction vector comprises:

determining an interpolation ratio of the current position of the target object between the first control point and the second control point based on the first control point and the second control point;

determining a distance between the first control point and the second control point, to obtain a control point distance; and determining, a motion trajectory of a current motion of the target object based on the first control point, the second control point, the interpolation ratio, the control point distance, the first direction vector, and the second direction vector, through the specified spline curve interpolation model as:

$P(U)=P_{i-1}+\lambda EU+(3P_i-3P_{i-1}-\lambda F-2\lambda E)U^2+(-2P_i+2P_{i-1}+\lambda F+\lambda E)U^3$, wherein P(U) is the motion trajectory of the target object, U is the interpolation ratio, $P_{i-1}$ is the first control point, $P_i$ is the second control point, λ is the control point distance, E is the first direction vector, and F is the second direction vector.

7. The method according to claim 6, wherein in a case that the first direction vector is equal to the second direction vector, the specified spline curve interpolation model is $P(U)=P_{i-1}+\lambda VU$, the motion trajectory of the target object on the motion track is a straight line, where V is the first direction vector or the second direction vector.

8. The method according to claim 1, wherein in a case that the first direction vector is equal to the second direction vector, the specified spline curve interpolation model is $P(U)=P_{i-1}+\lambda VU$, the motion trajectory of the target object on the motion track is a straight line, where V is the first direction vector or the second direction vector.

9. A device for determining a motion trajectory of a target object, comprising: one or more processors and a storage medium in which operation instructions are stored, wherein when the operation instructions stored in the storage medium are executed, the one or more processors perform steps of:

acquiring a first control point and a second control point on a motion track based on a current position of the target object on the motion track, wherein the first control point and the second control point are adjacent control points;

acquiring a first direction vector and a second direction vector, wherein the first direction vector is a unit direction vector at the first control point, and the second direction vector is a unit direction vector at the second control point;

acquiring a training spline curve interpolation model;

determining a training distance;

determining a first unit training vector and a second unit training vector through a derivative operation on the training spline curve interpolation model based on a first training control point, a second training control point, a third training control point, and a fourth training control point, wherein the first training control point, the second training control point, the third training control point, and the fourth training control point are control points arranged in the listed sequence on a training track;

determining a specified spline curve interpolation model based on the second training control point, the third training control point, the training distance, the first unit training vector, the second unit training vector, and the training spline curve interpolation model;

determining the motion trajectory of the target object on the motion track through the specified spline curve interpolation model based on the first control point, the second control point, the first direction vector, and the second direction vector; and controlling motion of the target object based on the motion trajectory.

10. The device according to claim 9, wherein when the processors perform determining the training distance, the processors perform:

determining a distance between the second training control point and the third training control point as the training distance, wherein when the processors perform determining the first unit training vector and the second unit training vector through the derivative operation on the training spline curve interpolation model based on the first training control point, the second training control point, the third training control point, and the fourth training control point, the processors perform:

determining a unit direction vector of a line connecting the first training control point and the third training control point as the first unit training vector; and determining a unit direction vector of a line connecting the first training control point and the fourth training control point as the second unit training vector.

11. The device according to claim 10, wherein when the processors perform determining the motion trajectory of the target object on the motion track through the specified spline curve interpolation model based on the first control point, the second control point, the first direction vector, and the second direction vector, the processors perform:

determining an interpolation ratio of a current position of the target object between the first control point and the second control point based on the first control point and the second control point;

determining a distance between the first control point and the second control point, to obtain a control point distance; and determining, a motion trajectory of a current motion of the target object based on the first control point, the second control point, the interpolation ratio, the control point distance, the first direction vector, and the second direction vector, through the specified spline curve interpolation model as:

$$P(U)=P_{i-1}+\lambda EU+(3P_i-3P_{i-1}-\lambda F-2\lambda E)U^2+(-2P_i+2P_{i-1}+\lambda F+\lambda E)U^3,$$

wherein P(U) is the motion trajectory of the target object, U is the interpolation ratio, $P_{i-1}$ is the first control point, $P_i$ is the second control point, $\lambda$ is the control point distance, E is the first direction vector, and F is the second direction vector.

12. The device according to claim 9, wherein when the processors perform determining the specified spline curve interpolation model based on the second training control point, the third training control point, the training distance, the first unit training vector, the second unit training vector, and the training spline curve interpolation model, the processors perform:

determining a parameter of the training spline curve interpolation model based on the second training control point, the third training control point, the training distance, the first unit training vector, and the second unit training vector; and determining the specified spline curve interpolation model based on the parameter of the training spline curve interpolation model and the training spline curve interpolation model.

13. The device according to claim 12, wherein when the processors perform determining the motion trajectory of the target object on the motion track through the specified spline curve interpolation model based on the first control point, the second control point, the first direction vector, and the second direction vector, the processors perform:

determining an interpolation ratio of a current position of the target object between the first control point and the second control point based on the first control point and the second control point;

determining a distance between the first control point and the second control point, to obtain a control point distance; and determining, a motion trajectory of a current motion of the target object based on the first control point, the second control point, the interpolation ratio, the control point distance, the first direction vector, and the second direction vector, through the specified spline curve interpolation model as:

$$P(U)=P_{i-1}+\lambda EU+(3P_i-3P_{i-1}-\lambda F-2\lambda E)U^2+(-2P_i+2P_{i-1}+\lambda F+\lambda E)U^3,$$

wherein P(U) is the motion trajectory of the target object, U is the interpolation ratio, $P_{i-1}$ is the first control point, P$_i$ is the second control point, λ is the control point distance, E is the first direction vector, and F is the second direction vector.

14. The device according to claim 9, wherein when the processors perform determining the motion trajectory of the target object on the motion track through the specified spline curve interpolation model based on the first control point, the second control point, the first direction vector, and the second direction vector, the processors perform:

determining an interpolation ratio of a current position of the target object between the first control point and the second control point based on the first control point and the second control point;

determining a distance between the first control point and the second control point, to obtain a control point distance; and determining, a motion trajectory of a current motion of the target object based on the first control point, the second control point, the interpolation ratio, the control point distance, the first direction vector, and the second direction vector, through the specified spline curve interpolation model as:

$P(U)=P_{i-1}+\lambda EU+(3P_i-3P_{i-1}-\lambda F-2\lambda E)U^2+(-2P_i+2P_{i-1}+\lambda F+\lambda E)U^3$, wherein P(U) is the motion trajectory of the target object, U is the interpolation ratio, P$_{i-1}$ is the first control point, P$_i$ is the second control point, λ is the control point distance, E is the first direction vector, and F is the second direction vector.

15. The device according to claim 14, wherein in a case that the first direction vector is equal to the second direction vector, the specified spline curve interpolation model is P(U)=P$_{i-1}$+λVU, the motion trajectory of the target object on the motion track is a straight line, where V is the first direction vector or the second direction vector.

16. The device according to claim 9, wherein in a case that the first direction vector is equal to the second direction vector, the specified spline curve interpolation model is P(U)=P$_{i-1}$+λVU, the motion trajectory of the target object on the motion track is a straight line, where V is the first direction vector or the second direction vector.

17. A non-transitory computer readable storage medium, storing computer executable instructions, wherein when the executable instructions are executed in a computer, the computer performs:

acquiring a first control point and a second control point on a motion track based on a current position of a target object on the motion track, wherein the first control point and the second control point are adjacent control points;

acquiring a first direction vector and a second direction vector, wherein the first direction vector is a unit direction vector at the first control point, and the second direction vector is a unit direction vector at the second control point;

acquiring a training spline curve interpolation model;

determining a training distance;

determining a first unit training vector and a second unit training vector through a derivative operation on the training spline curve interpolation model based on a first training control point, a second training control point, a third training control point, and a fourth training control point, wherein the first training control point, the second training control point, the third training control point, and the fourth training control point are control points arranged in the listed sequence on a training track;

determining a specified spline curve interpolation model based on the second training control point, the third training control point, the training distance, the first unit training vector, the second unit training vector, and the training spline curve interpolation model;

determining a motion trajectory of the target object on the motion track through the specified spline curve interpolation model based on the first control point, the second control point, the first direction vector, and the second direction vector; and controlling motion of the target object based on the motion trajectory.

* * * * *